United States Patent [19]

Pelosi

[11] Patent Number: 5,596,080
[45] Date of Patent: Jan. 21, 1997

[54] CROSSLINKING PROCESSES/AGENTS FOR ZEIN

[75] Inventor: Lorenzo F. Pelosi, Wilmington, Del.

[73] Assignee: E. I. Du Pont de Nemours and Company, Wilmington, Del.

[21] Appl. No.: 316,445

[22] Filed: Oct. 3, 1994

[51] Int. Cl.$^6$ .................................................. C07K 14/425
[52] U.S. Cl. ........................ 530/373; 530/370; 530/372; 264/126
[58] Field of Search ............................ 264/126; 530/373, 530/370, 372

[56] References Cited

U.S. PATENT DOCUMENTS

| | | | |
|---|---|---|---|
| 2,040,033 | 5/1936 | Sturken et al. | 530/373 |
| 2,134,760 | 11/1938 | Irey | 530/373 |
| 2,178,924 | 11/1939 | Sturken | 530/373 |
| 2,285,758 | 6/1942 | Sturken | 530/373 |
| 2,322,486 | 6/1943 | Swallen et al. | 530/373 |
| 2,375,103 | 5/1945 | Harrison | 530/373 |
| 2,427,503 | 9/1947 | Morgan | 530/373 |
| 2,429,214 | 10/1947 | Biehn et al. | 18/54 |
| 2,475,879 | 7/1949 | Cline | 18/54 |
| 2,519,978 | 8/1950 | Press | 18/54 |
| 2,521,704 | 9/1950 | Evans et al. | 18/54 |
| 2,521,738 | 9/1950 | McMeekin et al. | 18/54 |
| 3,497,369 | 2/1970 | Martin | 106/153 |
| 3,804,653 | 4/1974 | Morris et al. | 106/124 |
| 3,891,580 | 6/1975 | Morris et al. | 260/8 |
| 4,002,485 | 1/1977 | Hammer et al. | 106/136 |
| 4,002,710 | 1/1977 | Hammer et al. | 264/183 |
| 4,097,623 | 6/1978 | Hammer et al. | 427/230 |
| 4,104,444 | 8/1978 | Hammer et al. | 428/474 |
| 4,142,013 | 2/1979 | Hammer et al. | 428/36 |
| 5,260,396 | 11/1993 | Kroner et al. | 527/201 |
| 5,324,351 | 6/1994 | Oshlack et al. | 530/373 |

FOREIGN PATENT DOCUMENTS 0492652  9/1938  United Kingdom.

OTHER PUBLICATIONS

*Aldrich*; Aldrich Chem Co.; Milwaukee, Wisc.; (1990); pp. 657 & 787.

Croston, C.B. et al, *Industrial and Engineering Chemistry*, 37(12), 1194–1198 (1945).

*Primary Examiner*—W. Robinson H. Clark

[57] ABSTRACT

This invention provides a process for making crosslinked zein, comprising heating zein in the presence of water to a temperature of at least 130° C., with or without pressure, to induce crosslinking.

6 Claims, No Drawings

CROSSLINKING PROCESSES/AGENTS FOR ZEIN

BACKGROUND OF THE INVENTION

This invention relates to processes for crosslinking compositions containing the polymeric corn protein zein, thus increasing the strength and stability of articles made from such compositions.

Zein is a naturally occurring protein polymer, obtained as a product of industrial corn processing. Compared to most proteins, zein is characterized by a relative deficiency of hydrophilic groups. In zein, the high proportion of nonpolar and amide side chains accounts for the solubility of zein in organic solvents and its classification as a prolamine.

Zein is a globular protein in its native state. Most processes to make zein fibers involve, first hydrating the protein, realigning it as desired (e.g., by spinning), and finally stabilizing the new alignment by crosslinking. These processes most often start with an alkaline zein solution which is wet spun into acidic coagulating baths. After spinning, crosslinking can be induced by treatment in coagulating baths with formaldehyde, and subsequent further hardening or stabilizing treatments, typically using formaldehyde, followed by drawing stages to improve tenacity.

Croston et al., describe such a process in "Zein Fibers . . . Preparation by Wet Spinning", *Industrial and Engineering Chemistry*, 37 (1945) 1194–1198. Croston et al. call for a precuring bath of formaldehyde after fiber spinning, which was found to be necessary prior to the final stretching of the fiber tow.

Zein's chemical inertness and globular structure make molding articles difficult. U.S. Pat. No. 3,497,369, discloses a composition of zein, which is substantially dry and which upon the addition of warm water, forms a pliable plastic composition which may be pulled like taffy, molded, or worked with as modeling clay. The composition consists of zein and a small portion of a plasticizer such as glyceryl monoricinoleate. About 5 parts of plasticizer for every 75 parts of zein is most preferred.

This reference describes a process for making bristles from zein, wherein extruded zein fibers are cut into suitable lengths, treated with a chemical hardening agent, such as formaldehyde, and subsequently stretched and subjected to a second hardening treatment.

The environmental implications of using aldehydes as crosslinkers for zein, or of adding plasticizers to zein compositions, make such processes commercially undesirable today. The expense of treatment and disposal make production of useful zein fibers or articles unattractive. Thus, there is a need for environmentally friendly stabilizing agents for zein, to be used in production of zein fibers or articles. The present invention addresses such a need.

SUMMARY OF THE INVENTION

This invention provides a process for making crosslinked zein comprising heating zein in the presence of water to a temperature of at least about 130° C. to induce crosslinking.

This invention provides a process for making zein articles comprising:
(a) forming a mixture of zein with water having a viscosity and consistency such that it can be shaped into an article;
(b) shaping said mixture into an article;
(c) heating said article at a temperature of at least 130° C. for an effective period of time to form a crosslinked article.

This invention also provides a process for making zein articles comprising:
(a) forming a mixture of zein with an amino resin having a viscosity and consistency such that it can be shaped into an article;
(b) shaping said mixture into an article; and
(c) heating said mixture at a sufficient temperature for a period of time sufficient to form a crosslinked article.

This invention further provides a process for making zein articles comprising:
(a) providing a mixture of zein, hexamethylenetetramine, and a solvent for hexamethylenetetramine;
(b) evaporating the solvent to form a mixture having a viscosity and consistency such that it can be shaped into an article;
(c) shaping said mixture into an article; and
(d) exposing said article to an acidic medium for a sufficient time to induce crosslinking.

DETAILED DISCUSSION OF THE INVENTION

The first embodiment of this invention provides a process for preparing highly stable, water-resistant zein articles without the need for toxic chemical crosslinking agents. This embodiment thus avoids the need for crosslinking agents like formaldehyde. The inventor has identified an improved and simplified process in which water and heat are used to crosslink zein molecules in an article. The resulting zein articles are nontoxic and nonpolluting.

The process of the first embodiment of this invention usually, but not necessarily, involves molding in a closed mold, under pressure. However, other ways of making shaped articles also are feasible, including extrusion or coating the shapeable mixture on a substrate followed by heating. In each case, the process begins with making a shapeable mixture, i.e., a viscous mixture, of zein and water. This can be done at approximately 25°–40° C. Generally, the composition of this moldable mass can contain up to 67% by weight of water, provided there is at least about 5% by weight of water present. Preferably, the shapeable mass will contain about 10% to 40% of water by weight, most preferably about 30% of water by weight. The remaining composition by weight is zein, usually as a powder.

This zein/water mixture can be crosslinked, and thus solidified, by treating it with heat. A temperature of at least about 130° C. must be achieved, the preferred temperature being in the range of 140°–190° C., most preferably about 150° C. Articles can be formed by using pressure in addition to heat. Most frequently, the shapeable mixture is used to fill a mold which is then subjected to heat and pressure. After heating, the article is allowed to cool in the mold under pressure to below about 90° C. After releasing the pressure, the molded article is allowed to dry.

Inventor's process is based on the discovery that at a temperature of at least about 130° C., in the presence of water, zein will crosslink. Articles made by the process of this invention do not dissolve in 50% aqueous acetic acid and are highly water-resistant as shown by swelling tests in water both at room temperature and at 100° C. While it was generally considered in the past that insolubility of a zein composition in 90% alcohol was a proof that the zein composition was crosslinked, the present inventor has found that insolubility in 90% alcohol is not a good criterion for crosslinking. The composition may be insoluble in 90% alcohol but still not crosslinked, or at least not fully cross linked. Accordingly, the present inventor prefers to rely on the insolubility in 50% aqueous acetic acid. However, for the sake of comparison, solubility data for both solvent systems are given herein.

A second embodiment of this invention is a process which accomplishes crosslinking zein by the addition of a crosslinking agent to zein. The use of crosslinking agents according to the method of this invention is novel in that these agents have not previously been used to crosslink zein. Suitable crosslinking agents include multifunctional reagents such as amino resins (e.g., melamine resins, urea-formaldehyde resins) and hexamethylenetetramine (HMT).

Various methods can be used to employ the crosslinking agents of this invention. One method involves coating the zein particles with a crosslinking agent such as melamine-formaldehyde resin, by mixing zein with a small amount of melamine-formaldehyde resin, dissolved in a solvent, in a mechanical mixer or in a rotary evaporator. A suitable solvent for melamine-formaldehyde resin is methylene chloride. The solvent which is chosen must dissolve the desired crosslinking agent and evaporate rapidly. Heat is used to effect crosslinking. However, heat may or may not be required to effect crosslinking, depending on the reactivity of the melamine resin chosen. However, the use of a solvent is not always required, depending on the particular crosslinking agent used.

Preferably, crosslinking agents of this invention are simply added to a zein/water mixture. Melamine-formaldehyde resin is added to a zein/water mixture and then the mixture is subjected to heat and optionally pressure, substantially in the manner described for the first embodiment, above. However, when a solvent is used, an additional step of evaporating most of the solvent prior to crosslinking is preferred. If most of the solvent is not evaporated prior to crosslinking, it can leave voids in the resulting article which will weaken it. (If a porous article is desired, the solvent need not be completely evaporated.) The evaporation can be effected in many ways, e.g., by heating in an oven or by subjecting the material to a reduced pressure, or can even occur spontaneously during extrusion of the articles.

The next step is heating to crosslink the article. Since melamine resins can have varying reactivities, the amount of heat needed to crosslink will vary accordingly. Usually, heating for a few minutes at a temperature of at least 100° C., with or without pressure, is satisfactory. It normally should not be necessary to use temperatures in excess of 200° C., and a temperature within the range of about 130°–160° C. usually is satisfactory.

Hexamethylenetetramine (HMT) was found to be an acid-catalyzed crosslinking agent for zein. HMT can be dissolved in a solvent and the HMT/solvent mixture can be added to a zein mixture comprising the same solvent. Suitable solvents include dimethylformamide, and alcohol/water mixtures, specifically ethanol/water and methanol/water. An article can then be shaped, but the pH of the article must be lowered to the acid range (just below about 7.0) to effect crosslinking. This can be done in any convenient manner, including immersing the shaped article in an acidic bath. Prior to shaping, e.g., by molding or extruding, the major portion of any volatile solvent present in the composition, such as water/ethanol or water/methanol mixtures, preferably should be evaporated to prevent voids in the resulting article. This process, which employs HMT as a zein-crosslinking agent, is most effective for thin films or small-diameter molded or extruded articles. The acidic bath should comprise a nonsolvent for zein, with added acid, such as acetic or formic acid.

Zein powder can be commercially purchased (Freeman Industries, Inc., Tuckahoe, N.Y.).

Successful crosslinking is confirmed when the shaped article is not soluble in 50% aqueous acetic acid. On the other hand, the fact that the shaped article is insoluble in 90% ethanol does not necessarily prove that crosslinking has occurred, as will be shown below.

This invention is now illustrated by the following examples of certain representative embodiments thereof, where all percentages are by weight. Solubility data for the dry test bars produced in all examples are tabulated at the end of the experimental part.

EXAMPLE 1

ZEIN WITH WATER - 150° C.

The following were placed in a zip lock polyethylene bag and mixed by hand kneading: 5.0 g zein (purified) and 3.0 g of deionized water, at room temperature, approximately 25° C. The mold and polymer mix were placed in a press, heated to 150° C., for 22 minutes. Approximately 10,000 lbs (44,482 N) total force was used, which corresponds to approximately 4000 psi (27 MPa) for a 5 in. (12.7 cm)×½ in (1.27 cm) bar. The heat was then turned off and the mold was allowed to cool to 60° C. under pressure before removing the shaped article.

EXAMPLE 2

ZEIN WITH WATER - 130° C.

This experiment was carried out substantially as described in Example 1, except that the mold was heated to 130° C. for 10 minutes. The resulting bar was tested for solubility in 90% ethanol and in 50% acetic acid.

COMPARATIVE EXAMPLE A

ZEIN WITH WATER - 110° C.

This Example was conducted substantially according to the procedure of Example 1, except that the mold was heated to 110° C. for 10 minutes.

COMPARATIVE EXAMPLE B

ZEIN WITH WATER - 120° C.

This Example was conducted substantially according to the procedure of Example 1, except that the mold was heated to 120° C. for 10 minutes.

EXAMPLE 3

ZEIN WITH MELAMINE-FORMALDEHYDE RESIN - 10%

CROSSLINKING

Zein - Dry Polymer Preparation

Two glass jars, each with 50 g of regular grade zein and 500 ml of methylene chloride were placed on a roller mill to wash the polymer. The methylene chloride was changed twice, at about 2-hour intervals, using suction filtration. After the second change, the jars were left on the roller mill overnight, and the product was collected by suction filtration.

The recovered zein polymer was dried at 40° C. in a vacuum oven under nitrogen for about 50 hours.

Coating Polymer with Melamine-Formaldehyde Resin

An amount of 1.7 g of melamine-formaldehyde resin (Cargill 2347, Cargill, Inc., Wayzata, Minn.) was predissolved in methylene chloride in a 500 ml round bottom flask. Fifteen grams of zein (fine powder) was then added. The mixture was agitated on a rotary evaporator for 5–10 minutes at room temperature. The methylene chloride was then slowly evaporated until a free-flowing powder was obtained. The powder was placed under vacuum at room temperature to remove any residual methylene chloride. The coated powder was used to prepare a bar.

Bars were formed from zein polymer using a mold. A Carver Lab Press, Model C was used to apply heat and pressure to the mold. The bars were formed (using 2.0 g of material to fill the mold) by heating at 150° C. for 3 minutes at 10000 lbs (44,482 N) total force, approximately 4000 psi (27 MPa), and then cooling in the mold under pressure.

EXAMPLE 4

ZEIN WITH MELAMINE-FORMALDEHYDE RESIN - 5% CROSSLINK

A bar was formed in the manner described in Example 2, except that 0.8 g of melamine-formaldehyde resin was used.

EXAMPLE 5

ZEIN WITH MELAMINE-FORMALDEHYDE RESIN - 3% CROSSLINK

A bar was formed in the manner described in Example 2, except that 0.5 g of melamine-formaldehyde resin was used.

EXAMPLE 6

ZEIN WITH MELAMINE-FORMALDEHYDE RESIN - 1% CROSSLINK

A bar was formed in the manner described in Example 2 except that 0.15 g of melamine-formaldehyde resin was used.

EXAMPLE 7

ZEIN WITH HEXAMETHYLENETETRAMINE

Zein, 0.6 g, was dissolved in dimethylformamide (DMF), and 1 g of a 5% hexamethylenetetramine (HMT) in DMF was added. Small amounts of acetic acid and formic acid were added to the mixture, which caused crosslinking.

COMPARATIVE EXAMPLE C

ZEIN WITH WATER - NO HEAT

This Example was conducted substantially according to the process of Example 1, except that the mold was not heated.

COMPARATIVE EXAMPLE D

ZEIN (AS IS)

Untreated zein, 2.0 g, was molded into a bar as described in Example 2. The bar was yellowish in color.

COMPARATIVE EXAMPLE E

PURIFIED ZEIN

Zein was extracted with methylene chloride at reflux, then dried in vacuum at 40° C. Two grams of the resulting material were molded into a bar as described in Example 2. The bar was less colored

COMPARATIVE EXAMPLE F

BOILED ZEIN

Zein, 2.0 g, was boiled in water.

COMPARATIVE EXAMPLE G

VACUUM-DRIED ZEIN

The zein was vacuum dried prior to molding as described in Example 2.

TABLE

| ZEIN ARTICLES' SULUBILITIES* | | |
|---|---|---|
| Example Zein+ | Solubility 90% EtOH | Solubility 50% Acetic Acid |
| 1 - Water at 150° C. | I | I |
| 2 - Water at 130° C. | I | I |
| Comparative A - Water at 110° C. | I | S |
| Comparative B - Water at 120° C. | I | S |
| 3 - 10% MF | I | I |
| 4 - 5% MF | I | I |
| 5 - 3% MF | I | I |
| 6 - 1% MF | I | I |
| 7 - HMT | — | I |
| Comparative C - Water at room temp. | S | S |
| Comparative D - As is | S | S |
| Comparative E - Purified zein | S | S |
| Comparative F - Boiled 5 min. | I | S |
| Comparative G - Vacuum dried | S | S |

*I = insoluble
S = soluble
MF = Melamine-formaldehyde resin

What is claimed is:

1. A process for making crosslinked zein, said process comprising crosslinking zein by means of heating zein in the presence of water, which is the sole crosslinking agent, to a temperature of at least about 130° C., the initial amount of water being about 5–67 weight percent of the composition, thereby avoiding the need for toxic chemical crosslinking agents.

2. The process of Claim 1 in which steps (b) and (c) are conducted in a closed mold.

3. A process for making zein articles comprising:
   (a) forming a mixture of zein with water, which is the sole crosslinking agent, comprising approximately 5–67% by weight of water, having a viscosity and consistency such that it can be shaped into an article;
   (b) shaping said mixture into an article; and (c) crosslinking said mixture by means of heating said article at a temperature of at least 130° C. to form a crosslinked article, thereby avoiding the need for toxic chemical crosslinking agents.

4. The process according to Claim 3 wherein the mixture of zein and water contains from about 10% to about 40% by weight water.

5. The process according to Claim 3 wherein step (c) is conducted at a temperature ranging from about 140° C. to about 190° C.

6. An article made according to the process of Claim 3.

* * * * *